(12) United States Patent
Labonville et al.

(10) Patent No.: US 8,437,639 B2
(45) Date of Patent: *May 7, 2013

(54) OPERATOR INPUT DEVICE FOR A ROBOTIC SURGICAL SYSTEM

(75) Inventors: Gerard J Labonville, San Jose, CA (US); Alan E. Loh, Los Altos, CA (US); David W. Bailey, Redwood City, CA (US); Brett J. Lockyer, San Jose, CA (US)

(73) Assignee: Intuitive Surgical Operation, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/292,734

(22) Filed: Nov. 9, 2011

(65) Prior Publication Data

US 2012/0051753 A1 Mar. 1, 2012

Related U.S. Application Data

(63) Continuation of application No. 12/242,275, filed on Sep. 30, 2008, now Pat. No. 8,073,335.

(51) Int. Cl.
*H04B 10/22* (2006.01)

(52) U.S. Cl.
USPC .......................................... 398/114; 250/551

(58) Field of Classification Search .................. 398/114; 250/551

See application file for complete search history.

(56) References Cited

U.S. PATENT DOCUMENTS

| | | | |
|---|---|---|---|
| 5,272,350 A | 12/1993 | Solari et al. | |
| 5,691,687 A | 11/1997 | Kumagai et al. | |
| 5,712,552 A | 1/1998 | Hirai et al. | |
| 5,818,188 A | 10/1998 | Hirai et al. | |
| 6,218,924 B1 | 4/2001 | Zabler et al. | |
| 6,424,885 B1 | 7/2002 | Niemeyer et al. | |
| 6,587,750 B2 | 7/2003 | Gerbi et al. | |
| 6,714,839 B2 | 3/2004 | Salisbury, Jr. et al. | |
| 6,915,584 B2 | 7/2005 | Skerka et al. | |
| 6,950,633 B2 | 9/2005 | Kojima et al. | |
| 8,073,335 B2 * | 12/2011 | Labonville et al. | 398/114 |
| 2008/0147089 A1 | 6/2008 | Loh et al. | |

OTHER PUBLICATIONS

Legranger, J. et al., "Comparison of Two Optimal Rotary Transformer Designs for Highly Constrained Applications," IEEE 2007 International Electric Machines & Drives Conference (IEMDC '07), May 3-5, 2007, vol. 2, pp. 1546-1551.

McLyman, Col. William T., "Rotary Transformer," pp. 1-4, 1996, Pub. John Wiley; Internet: http://trs-new.jpl.nasa.gov/dspace/handle/2014/27360.

Papastergiou Konstantinos D., "A Power Converter with a Rotating Secondary Stage for an Airborne Radar System," 2005, 272 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Leslie Pascal

(57) ABSTRACT

A device for receiving data from a rotatable source includes a primary winding of a rotary transformer fixed to a support structure and connected to an electric power source. A secondary winding is rotatably supported by the support structure. An axial passage extends through the primary and secondary windings. An optical data transmitter is connected to the secondary winding. The optical data transmitter is rotatably supported by the support structure and aligned to transmit data through the axial passage in the rotary transformer. The secondary transformer winding provides power to the optical data transmitter without physical contact. An optical data receiver fixed to the support structure receives data from the optical data transmitter transmitted through the axial passage in the rotary transformer without physical contact. The transmission of power and data without physical contact allows the data source to rotate continuously.

11 Claims, 7 Drawing Sheets

OPERATOR INPUT DEVICE FOR A ROBOTIC SURGICAL SYSTEM

CROSS REFERENCE TO RELATED APPLICATIONS

This application is a continuation of application Ser. No. 12/242,275, filed Sep. 30, 2008, which is hereby incorporated by reference in its entirety.

BACKGROUND

1. Field

This invention relates to data input devices, and more particularly, provides a master controller which may be used for directing movements of a robot and which is particularly useful for robotically enhanced surgery.

2. Background

In robotically assisted surgery, the surgeon typically operates a master controller to remotely control the motion of surgical instruments at the surgical site. The controller may be separated from the patient by a significant distance (e.g., across the operating room, in a different room, or in a completely different building than the patient). Alternatively, a controller may be positioned quite near the patient in the operating room. Regardless, the controller will typically include one or more hand input devices.

These hand input devices are coupled by a servo mechanism to the surgical instrument. More specifically, servo motors move a manipulator or "slave" supporting the surgical instrument based on the surgeon's manipulation of the hand input devices. During an operation, the controller may employ, via the robotic surgery system, a variety of surgical instruments such as tissue graspers, needle drivers, electrosurgical cautery probes, etc. Each of these structures performs functions for the surgeon, for example, holding or driving a needle, grasping a blood vessel, or dissecting, cauterizing, or coagulating tissue.

To deliver the full potential of this new form of surgery, the robotic system will preferably allow movement of the end-effector in both position and orientation. Directing such robotic input is much easier when the surgeon is able to move the hand input device with motions that correspond to the desired motions of the end-effector. Hence, it would be desirable to provide hand input devices which can move in three-dimensional space, and which can also change in orientation about three axes.

In particular, the ability to control a twisting motion (roll) with the fingers about one of the axes is an important motion. A rotatable handle may be used by the operator to control twisting motions of a surgical instrument. Further, it is desirable to provide additional operator inputs, such as switches to actuate a surgical instrument, such as a cautery probe, and grip controls to open and close a surgical instrument such as forceps or scissors. These additional operator and grip controls may be placed on the rotatable handle.

The placement of operator inputs on the rotatable handle requires that the input from the controls be transmitted through a rotating joint. Slip rings may be used to transmit the data, but slip rings are difficult to maintain and may introduce noise into the data signals, which could have undesirable consequences in the context of a robotic surgery. A slack wire cable provides reliable data communication but limits the rotational freedom of the handle, which adds an undesirable limitation on the freedom of the surgeon to direct the surgical instrument. Further, any operator input device needs to be compact and relatively light weight to increase the device's agility and minimize its constraints on the surgeon's ability to manipulate the surgical instrument.

In light of the above, it would be desirable to provide an improved operator input device for a robotic surgical apparatus.

SUMMARY

A device for receiving data from a rotatable source includes a primary winding of a rotary transformer fixed to a support structure and connected to an electric power source. A secondary winding is rotatably supported by the support structure. An axial passage extends through the primary and secondary windings. An optical data transmitter is connected to the secondary winding. The optical data transmitter is rotatably supported by the support structure and aligned to transmit data through the axial passage in the rotary transformer. The secondary transformer winding provides power to the optical data transmitter without physical contact. An optical data receiver fixed to the support structure receives data from the optical data transmitter transmitted through the axial passage in the rotary transformer without physical contact. The transmission of power and data without physical contact allows the data source to rotate continuously. An embodiment of the device may be used as an input device for a robotic surgical instrument that includes an operator input on a handle that is rotatably supported by the support structure.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known devices, structures and techniques have not been shown in detail in order not to obscure the understanding of this description.

Figure 1:
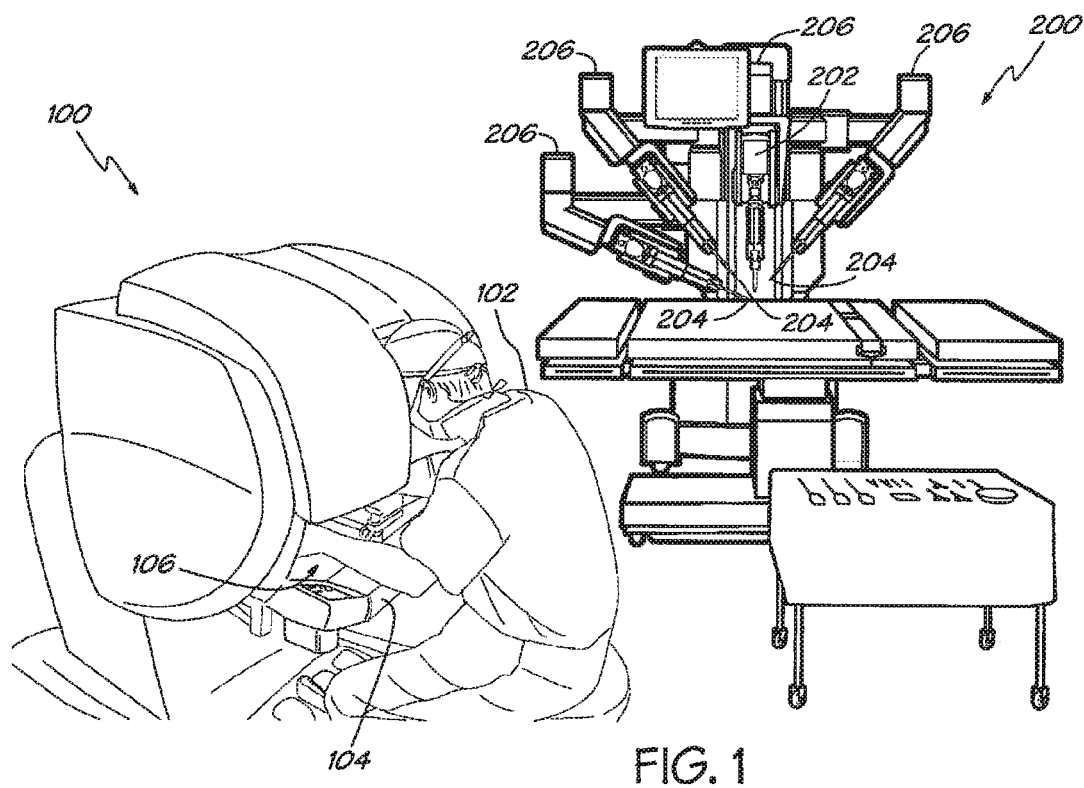
FIG. 1 is a perspective view of a master control workstation and a manipulator system for robotically moving a plurality of minimally invasive surgical instruments.
Figure 2:
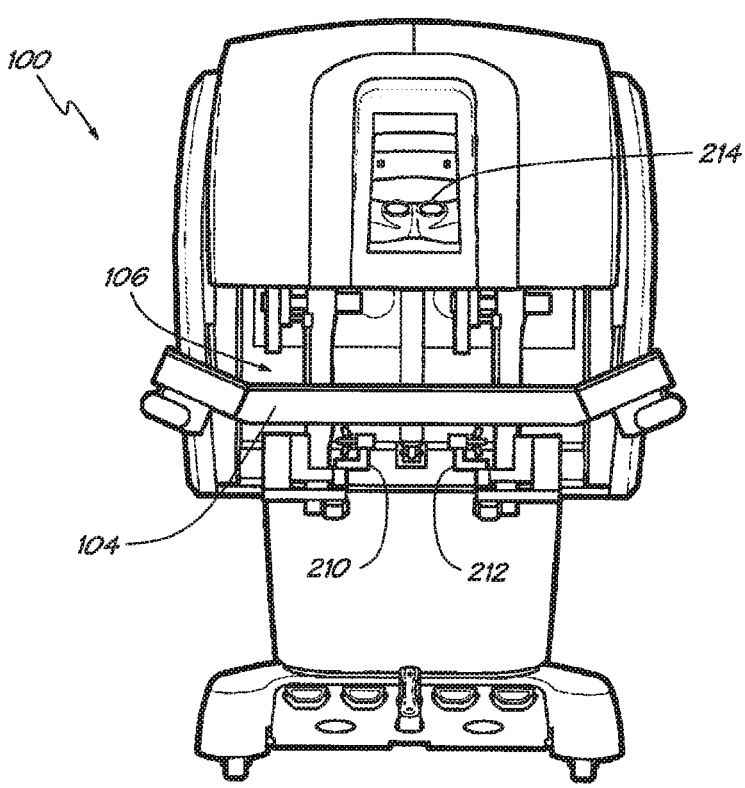
FIG. 2 is another perspective view of the master control workstation shown in FIG. 1.

Referring to FIG. 1 of the drawings, a master control workstation or surgeon's console of a minimally invasive telesurgical system is generally indicated by reference numeral 100. The workstation 100 includes a viewer 214 (shown in FIG. 2) where an image of a surgical site is displayed in use. A support 104 is provided on which an operator 102, typically a surgeon, can rest his or her forearms while gripping two master controls 210, 212 (shown in FIG. 2), one in each hand. The master controls are positioned in a workspace 106 disposed inwardly beyond the support 104. When using the workstation 100, the surgeon 102 typically sits in a chair in front of the workstation, positions his or her eyes in front of the viewer and grips the master controls 210, 212 one in each hand while resting his or her forearms on the support 104.

FIG. 1 also shows a patient side cart or surgical manipulator system 200 of the telesurgical system. In use, the cart is positioned close to a patient for surgery, and it is then normally caused to remain stationary until the surgical procedure has been completed. Manipulator system 200 typically includes robotic arm assemblies 206. One of the robotic arm assemblies is arranged to hold an image capturing device, e.g., an endoscope 202, or the like, which is coupled to the display of the workstation. Each of the other arm assemblies 206 may include a surgical tool 204 having a surgical end effector for treating tissue.

The robotic arms 206 will move and articulate the surgical tools 204 in response to the motions of the master controls 210, 212 at the workstation 100, so that the surgeon 102 can direct surgical procedures at internal surgical sites through minimally invasive surgical apertures. The workstation 100 is typically used within an operating room with the cart 200, but it can be positioned remotely from the cart, even miles away.

Figure 3:
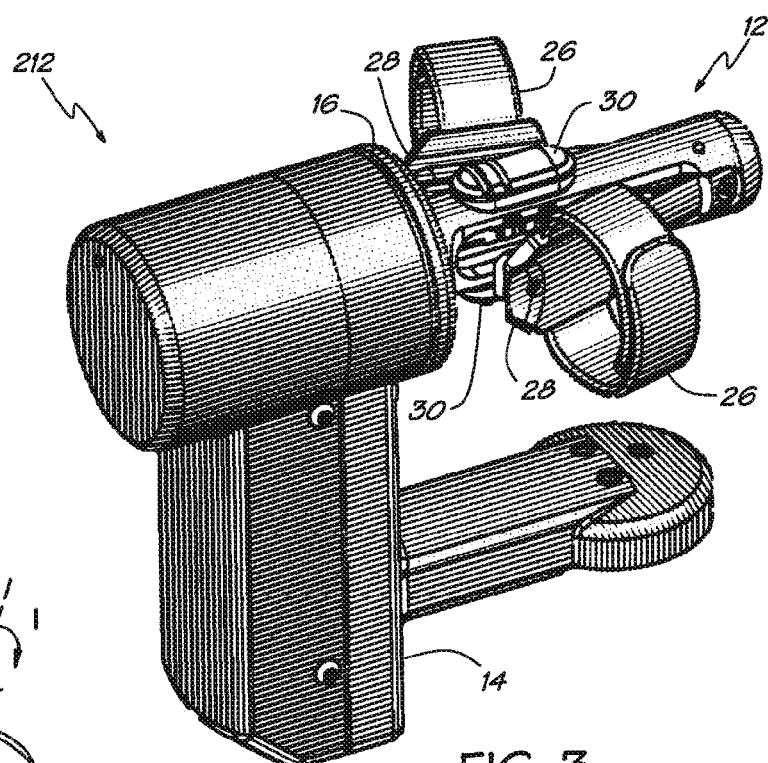
FIG. 3 is a perspective view of an operator input device used in the master control workstation shown in FIG. 2.
Figure 4:
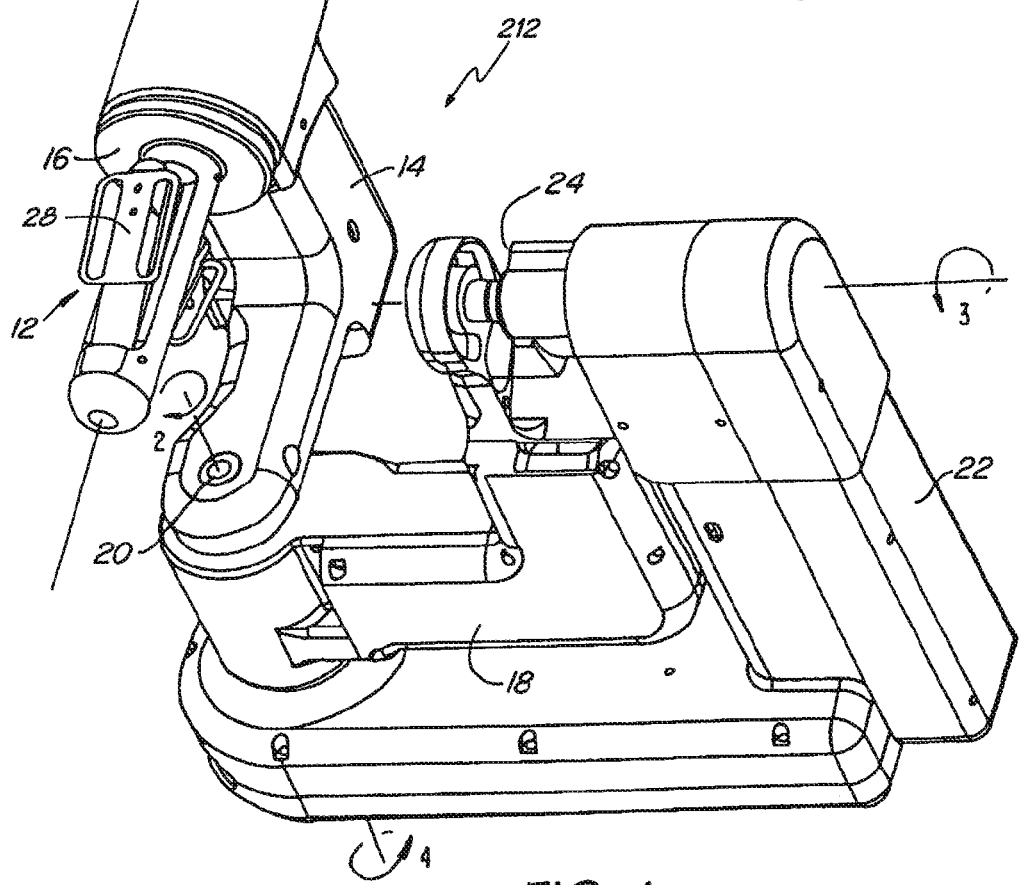
FIG. 4 is another perspective view of the operator input device shown in FIG. 3.

Referring now to FIGS. 3 and 4, each master controller 210, 212 includes a four degree of freedom gimbal or wrist that allows rotation of an actuatable handle 12 about three axes—axis 1, axis 2, and axis 3 in FIG. 4.

In the embodiment of the invention shown, the handle 12 is coupled to a first elbow-shaped link 14 by a first rotatable joint 16 that permits continuous rotation of the handle. The first link 14 is coupled to a second elbow-shaped link 18 by a second pivotal joint 20. The second link 18 is pivotally coupled to a third elbow-shaped link 22 by a third pivotal joint 24. The third link 22 is pivotally coupled to a platform (not shown) such that the third link can rotate with respect to the platform about axis 4 to provide a fourth degree of rotational freedom. The fourth degree of rotational freedom is redundant but it allows the second and third links 18, 22 to be positioned to avoid interfering with the operator's that is grasping the handle 12. The platform is supported to provide three degrees of translational freedom. Thus each master controller 210, 212 will generally allow movement of the handle 12 within the workspace 106 with a plurality of degrees of freedom, typically with six degrees of freedom, three rotational degrees of freedom and three translational degrees of freedom. This allows the actuatable handle 12 to be moved to any position and any orientation within its range of motion.

The actuatable handle 12 includes grip actuators 28 and/or switches 30 to allow the operator to actuate the surgical tool 204 being positioned by the motion of the handle. Finger loops 26 are attached to the handle 12 to prevent the operator's fingers from slipping on the handle.

Figure 5:
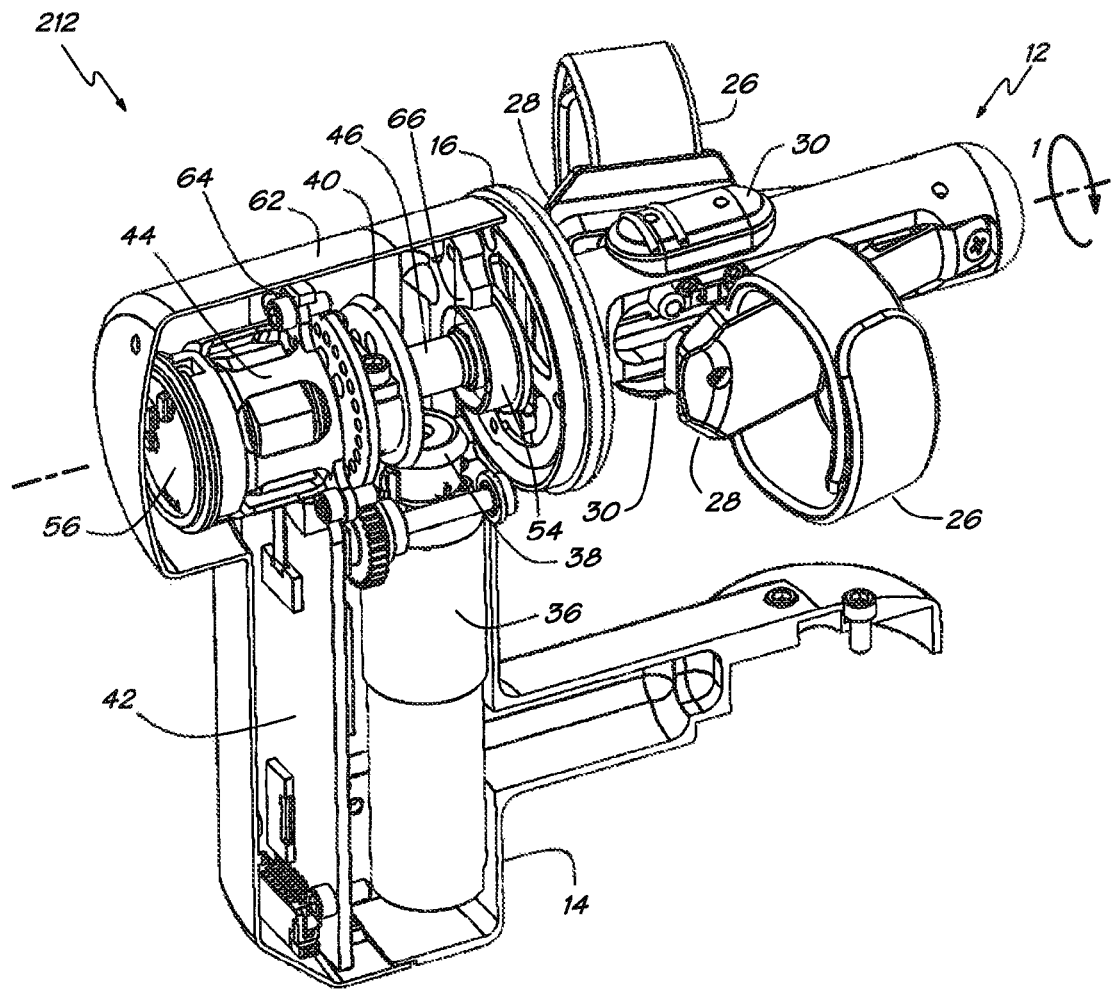
FIG. 5 is a cut-away view of the operator input device shown in FIG. 3.
Figure 6:
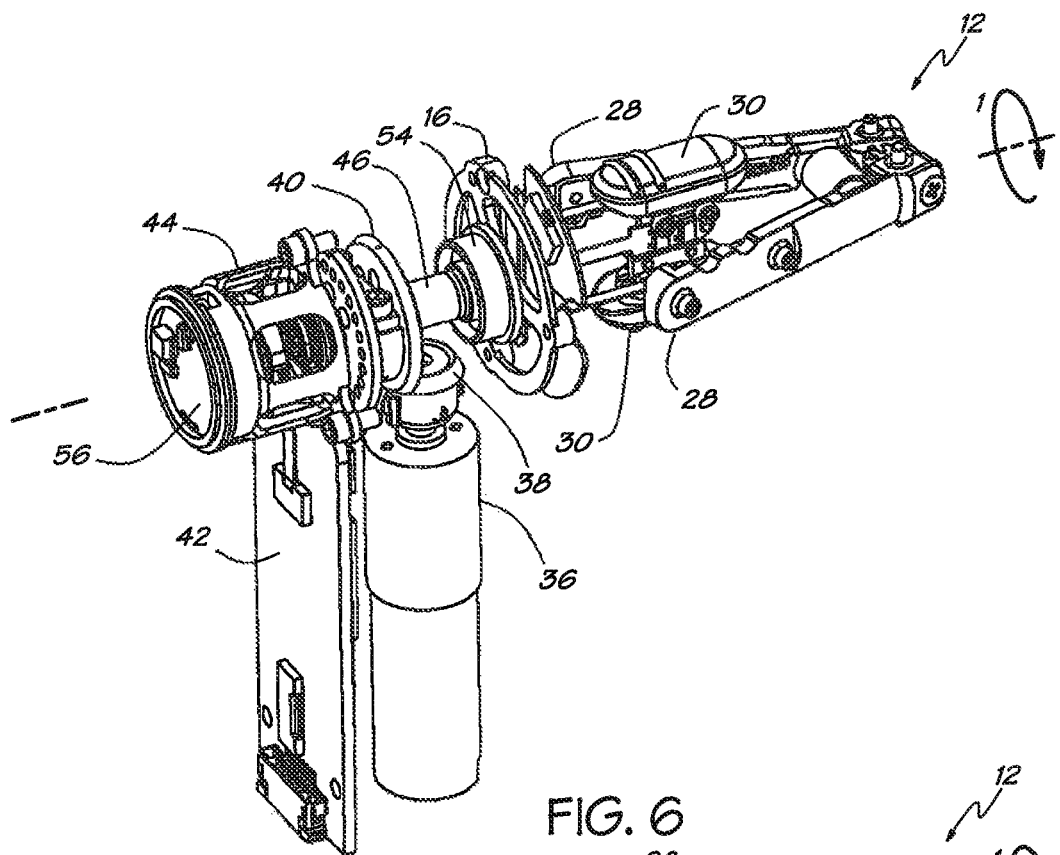
FIG. 6 is an interior view of the operator input device shown in FIG. 3.
Figure 7:
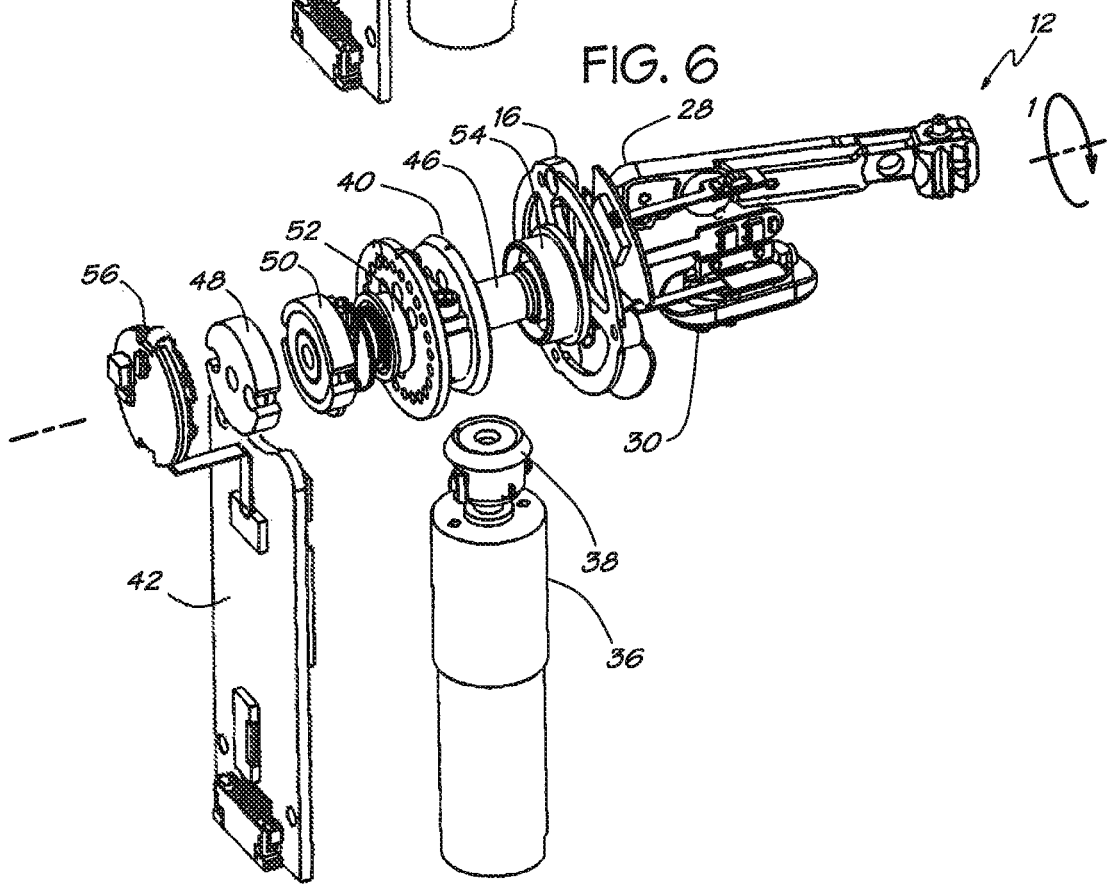
FIG. 7 is an exploded view of the operator input device shown in FIG. 6.

FIGS. 5 through 7, are views of components contained within the actuatable handle 12 and the first link 14. An important aspect of the invention is that it provides continuous rotation of a roll input in a compact assembly suitable for use in an input device for a robotic surgical instrument. Views with various components omitted are provided to allow the different elements of an embodiment of the invention to be seen. FIG. 5 shows the outer portion of the first link 14 cut away so that the components contained within the first link can be seen. FIG. 6 shows the components contained within the first link. FIG. 7 shows the components in an exploded view, with some components omitted to allow certain aspects to be seen more clearly.

Referring to FIGS. 5 through 7, the first link 14 is a hollow structure that encloses mechanical components and electronics that support the actuatable handle 12. The hollow structure of the first link 14 is of two or more parts to facilitate assembly of the first link and the components contained therein. The first link 14 includes bulkhead structures 64, 66 to which internal components are attached.

The actuatable handle 12 includes a structure 16 that supports one or more operator inputs such as switches 30 and grip controllers 28. The operator inputs may provide on/off control or a continuous range of control. For example, the grip controllers 28 may provide a range of input values that allows the surgical tool 204 to be moved between opened and closed positions by tracking the position of the grip controllers 28. A switch may have two or more positions to provide either on/off input or a selection based on the switch position. A continuous input may be used to provide on/off control or a discrete number of selections.

The support structure 16 is coupled to a shaft 46 that rotates within one or more bearings 52, 54. The shaft 46 also supports electronic components 50 that couple the input signals from the grip actuators 28 and/or switches 30 to the master control workstation as will described more fully below. The bearings 52, 54 are supported by the bulkhead structures 64, 66 of the first link 14 so that the actuatable handle 12 rotates freely about a first axis 1 with respect to the first link.

Additional components may be fixed to the bulkhead structures 64, 66 of the first link 14. For example, a motor 36 is fixed to the first link 14. The motor 36 is coupled to the handle 12 by beveled gears 38, 40. The motor 36 rotates the handle 12 about the first axis 1 to set an orientation of the handle to correspond to an orientation of the surgical tool 204 and/or provide haptic feedback for the rotational force being applied. To sense an angular position of the handle 12 about the first axis 1, an encoder and/or a potentiometer is coupled to the motor 36. Electronic components 42, 56, 48 are fixed to the bulkhead structures 44, 64 of the first link 14 and coupled to the input signals from the electronic components 50 that are rotatably supported by the actuatable handle 12 as will described more fully below.

Figure 8:
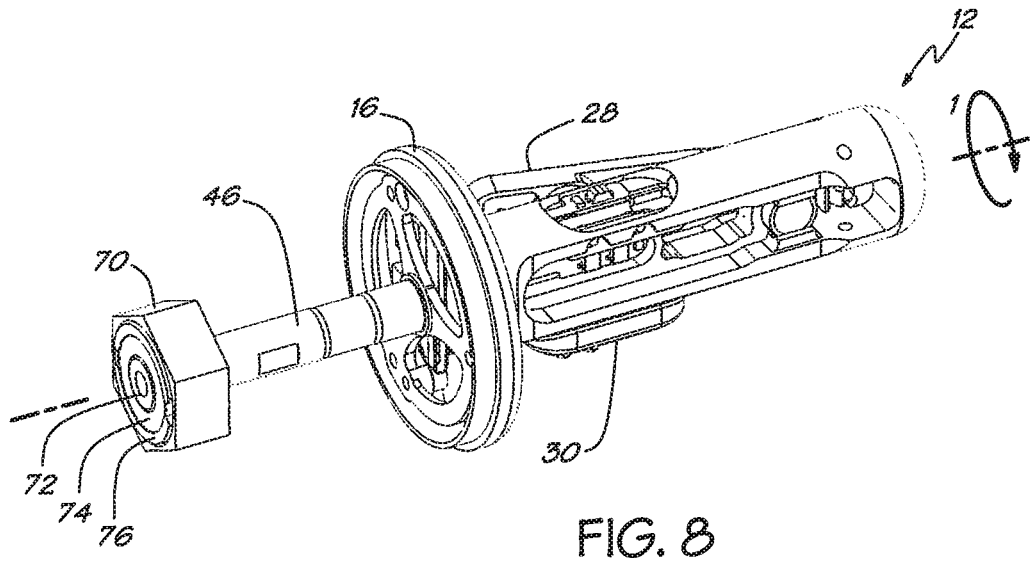
FIG. 8 is a perspective view of the handle portion of the input device of FIG. 3.
Figure 9:
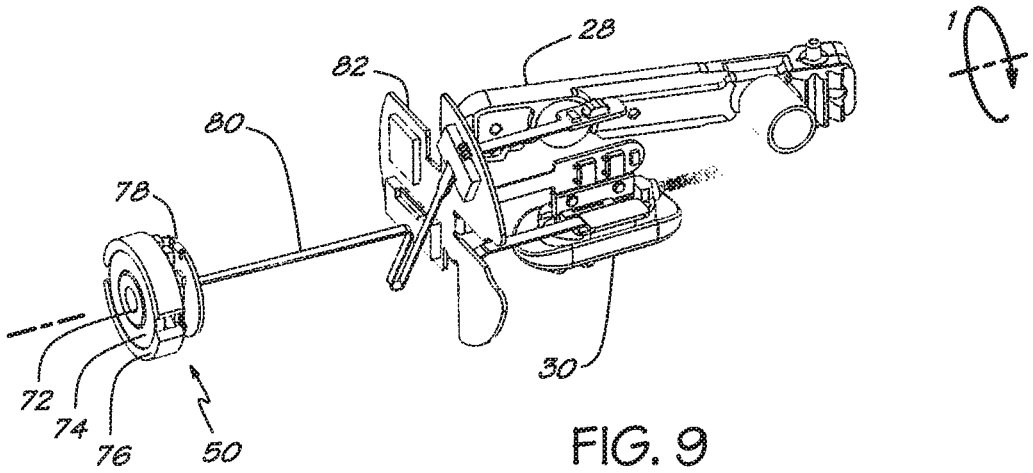
FIG. 9 is a perspective view of the handle portion of the input device of FIG. 3 with some exterior components removed.
Figure 10:
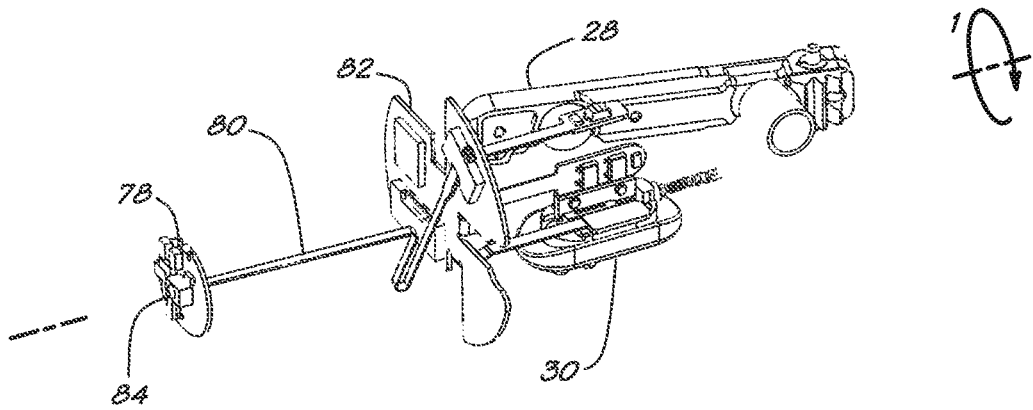
FIG. 10 is a perspective view of the handle portion of the input device of FIG. 3 with additional exterior components removed.

Referring now to FIGS. 8 through 10, components contained within the actuatable handle 12 are assembled and supported such that these components rotate as a unit about axis 1, the axis of rotation for the handle. A support structure 70, fixed to the end of the shaft 46, supports the electronic components 50 that receive the input signals from the grip actuators 28 and/or switches 30. As best seen in FIGS. 9 and 10, in which some of the outer structures are not shown, the grip actuators 28 and/or switches 30 are electrically coupled to electronics 82 that condition and/or encode the operator input as electrical signals.

The operator input signals are electrically coupled to signal generator electronics 78, 82 that generate a signal that is provided to an optical data transmitter 84 to optically transmit an encoded representation of the operator input. A rotary pot core half 76 is fixed to the handle 12 by the electronic component support structure 70, which is fixed to the end of the shaft 46. The rotary pot core half 76 has an open face, an opposing closed face, and an axial passage 72 between the open face and the closed face. A secondary transformer winding 74 is mounted in the rotary pot core half 76. The secondary transformer winding 74 provides electric power to the electronics 78, 82. The optical signal from the optical data transmitter 84 is directed through the axial passage 72 of the rotary pot core half 76. The cable 80 that connects the electronics passes through an axial opening in the shaft 46 that rotatably supports the handle 12.

Figure 11:
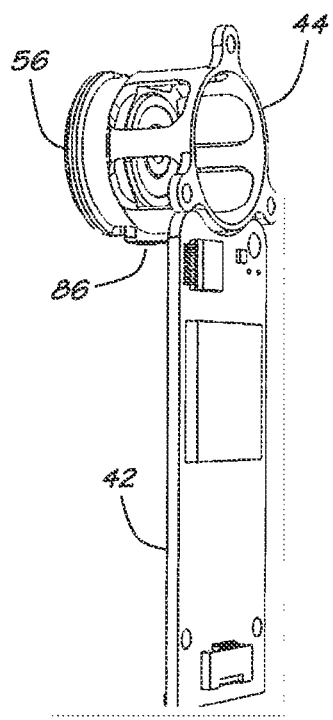
FIG. 11 is a perspective view of electronic components in the link portion of the input device of FIG. 3.
Figure 12:
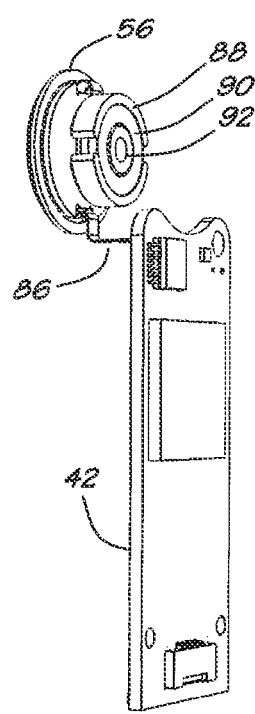
FIG. 12 is a perspective view of electronic components in the link portion of the input device of FIG. 3 with some exterior components removed.
Figure 13:
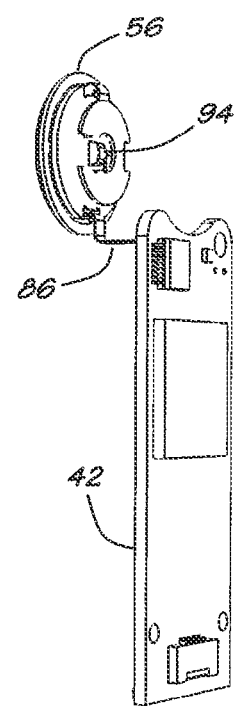
FIG. 13 is a perspective view of electronic components in the link portion of the input device of FIG. 3 with additional exterior components removed.

Referring now to FIGS. 11 through 13, components contained within the first link 14 are assembled and supported such that these components are fixed with respect to the first link. A support structure 44 fixes electronic components 56 to the bulkhead 64 of the first link 14. Additional electronic components are electrically coupled by a cable 86 and directly fixed to the bulkhead 64 of the first link 14.

As best seen in FIG. 12, a stationary pot core half 88 is fixed to the support structure 44 with the electronic components 56. The stationary pot core half 88 has an open face, an opposing closed face, and an axial passage 92 between the open face and the closed face. A primary transformer winding 90 is mounted in the stationary pot core half and connected to an electric power source (not shown). An optical data receiver 94 (FIG. 13) is supported adjacent the closed face of the stationary pot core half 88.

Figure 14:
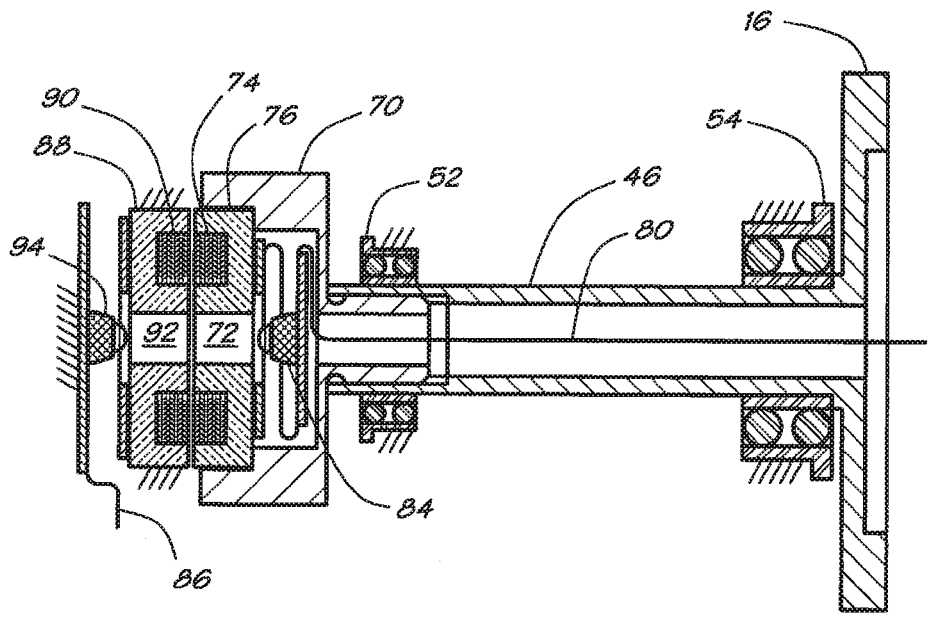
FIG. 14 is a cross-section view of a portion of the input device of FIG. 3 taken through the axis of rotation of the handle portion.

FIG. 14 shows a cross-section of a portion of the input device taken along axis 1 of the handle 12. The optical data transmitter 84 and the optical data receiver 94 are aligned such that the optical data is transmitted substantially along the axis of rotation of the handle 12 through the passages 92, 72 in the stationary and rotary pot core halves 88, 76. The primary and secondary windings 90, 74 form a rotary transformer. The stationary and rotary pot core halves 88, 76 are also part of the rotary transformer to increase the efficiency of the transformer.

The stationary and rotary pot core halves 88, 76 are coaxial and concentric with the axis of rotation of the handle 12. The primary and secondary windings 90, 74 of the rotary transformer are configured so that rotation of the secondary winding by rotation of the handle does not affect the operation of the transformer that they form. The open faces of the pot core halves face one another and the primary and secondary transformer windings 90, 74 are in close proximity so that a switched current in the primary winding is magnetically coupled to the secondary winding.

Figure 15:
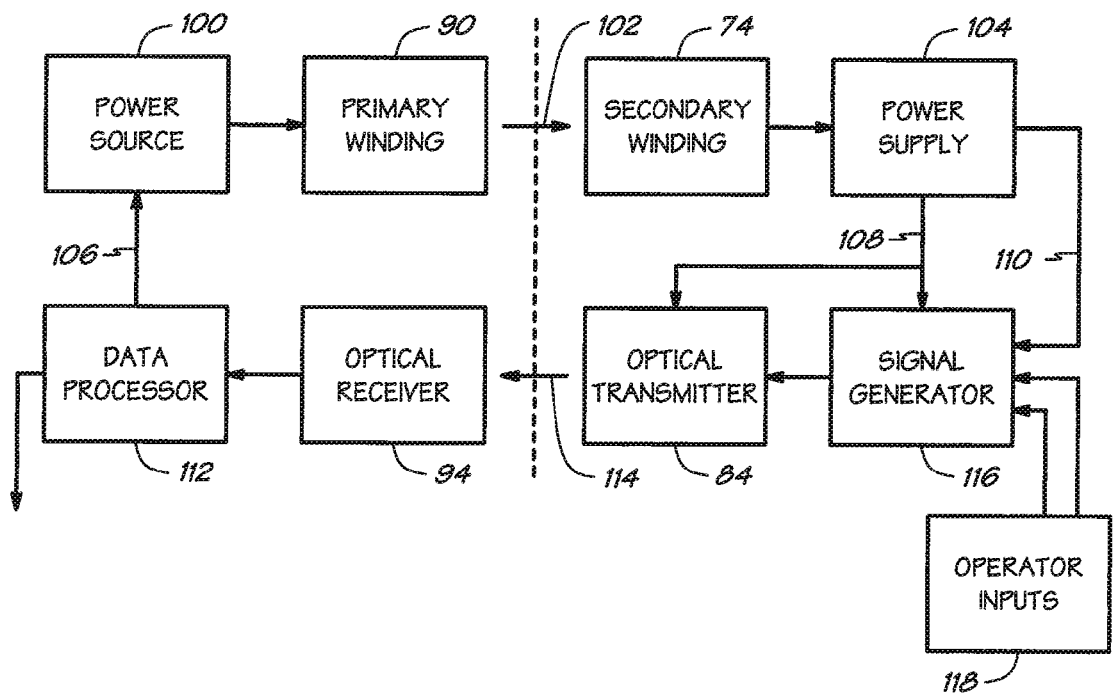
FIG. 15 is a block diagram showing electrical, magnetic, and optical connections of the input device of FIG. 3.

FIG. 15 is a block diagram showing electrical, magnetic, and optical connections of the input device. Components that are fixed to the support structure, which are shown to the left of the vertical dashed line, are not physically connected to components that are fixed to the handle, which are shown to the right of the vertical dashed line. The vertical dashed line represents an air gap in the rotary joint that couples the handle to the support structure. By eliminating a physical connection between the components in the support structure and the handle, the handle is made freely rotatable.

A power source 100 is connected to the primary winding 90 of the rotary transformer. The power source 100 and the primary winding 90 are fixed to the support structure. The primary winding 90 is magnetically coupled 102 to the secondary winding 74 of the rotary transformer. The secondary winding 74 is coupled to the power supply 104. The secondary winding 74 and the power supply 104 are fixed to the handle. The power supply provides power 108 for the signal generator 116 and the optical transmitter 84 and may also power other devices fixed to the handle.

The operator inputs 118 are coupled to the signal generator 116 to generate an encoded digital signal that represents the operator input. A power sensing signal 110 is also connected to the signal generator 116 so that the encoded digital signal also includes a representation of the voltage being provided by the power supply 104. The optical transmitter 84 optically transmits 114 the encoded digital signal to the optical receiver 94 that is fixed to the support structure.

A data processor 112 receives the encoded digital signal from the optical receiver 94 and processes the signal to provide the encoded information to the robotic surgical system. The data processor 112 provides a decoded representation 106 of the power sensing signal 110 to the power source 100. The power source adjusts the electrical power provided to the primary winding 90 of the rotary transformer according to the decoded representation 106 of the power sensing signal 110.

Embodiments of the invention provide an input device for robotic surgical techniques. The input device has a rotatable handle supporting operator input devices. Data from the operator inputs is transmitted optically across a freely rotatable joint by a rotary transformer. Electrical power form a power source is magnetically coupled to the optical data transmitter in the freely rotatable handle. Data from the power supply in the rotatable handle is transmitted optically to the power source to provide closed loop control of the power supply in the freely rotatable handle. The optical data path is along the axis of rotation of the rotary transformer to provide a compact assembly suitable for delicate operator inputs from the surgeon controlling the robotic surgical system.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. An operator input device comprising:
a support structure;
a rotary transformer having a primary winding fixed to the support structure and electrically connected to an electric power source, a secondary winding rotatably supported by the support structure, and an axial passage through the primary and secondary windings;
an optical data transmitter connected to the secondary winding, the optical data transmitter rotatably supported by the support structure and aligned to transmit data through the axial passage in the rotary transformer;
an optical data receiver fixed to the support structure and aligned to receive data from the optical data transmitter;

a signal generator rotatably supported by the support structure and electrically connected to the secondary transformer winding and to the optical data transmitter, the signal generator receiving power from the secondary transformer winding and generating data to be transmitted by the optical data transmitter;

a bearing supported by the support structure;

a tube rotatably supported by the bearing, the tube having a proximal end connected to the signal generator and a distal end connected to the secondary winding; and a wire that electrically connects the signal generator to the secondary winding, the wire passing through the tube from the proximal end to the distal end.

2. The input device of claim 1, wherein the signal generator generates a voltage signal to be transmitted by the optical data transmitter in response to the voltage provided by the secondary transformer winding.

3. The input device of claim 2, wherein the power source is connected to the optical data receiver, the power source being turned on and off in response to the voltage signal received by the optical data receiver.

4. The input device of claim 1, wherein the rotary transformer further includes a pot core, the primary winding being fixed in a first half of the pot core that is fixed to the support structure, the secondary winding being fixed in a second half of the pot core that is rotatably supported by the support structure, and the pot core providing the axial passage through the primary and secondary windings.

5. A method of providing data from a rotatable source, the method comprising:

generating data with a signal generator that is rotatably supported by a support structure;

coupling an electrical power source between a primary coil and a secondary coil, the primary coil fixedly supported by a support structure and connected to the electrical power source, the secondary coil rotatably supported by the support structure and connected to provide power to the signal generator;

optically transmitting data from the signal generator to an optical data receiver with an optical data transmitter, the optical data receiver fixed on the support structure, the optical data transmitter fixed on the secondary coil, the optical transmission directed through an axial passage through the primary and secondary coils;

generating a voltage signal in response to a voltage provided by the secondary coil; and multiplexing the voltage signal with the data from the signal generator.

6. The method of claim 5, further comprising turning the electrical power source on and off in response to the voltage signal received by the optical data receiver.

7. A device for providing data from a rotatable source, the device comprising:

means for generating data, the data generating means rotatably supported by a support structure;

means for receiving electrical power, the electrical power receiving means rotatably supported by the support structure and connected to the data generating means;

means for optically transmitting data, the optically transmitting means fixed on and connected to the electrical power receiving means, the optically transmitting means having an optical path directed through an axial passage toward a means for receiving optical data fixed on the support structure;

means for generating a voltage signal in response to a voltage provided by the electrical power receiving means; and means for multiplexing the voltage signal with data generated by the data generating means.

8. The device of claim 7, further comprising means for turning an electrical power source on and off in response to the voltage signal received by the means for receiving optical data.

9. An input device comprising:

a support structure;

a stationary pot core half fixed to the support structure and holding a primary transformer winding connected to an electric power source, the stationary pot core half having a first axial passage;

an optical data receiver fixed to the support structure adjacent the stationary pot core half;

a rotating structure that is rotatably supported by the support structure and is rotatable about an axis of rotation;

a rotary pot core half fixed to the rotating structure facing the stationary pot core half and holding a secondary transformer winding, the rotary pot core half having a second axial passage;

a signal generator fixed to the rotating structure and connected to the secondary transformer winding;

an optical data transmitter fixed to the rotating structure on the axis of rotation, the optical data transmitter connected to the secondary transformer winding to receive power and to the signal generator to transmit data from the signal generator through the first and second axial passages to the optical data receiver;

a signal generator fixed to the rotating structure and electrically connected to the secondary transformer winding and to the optical data transmitter, the signal generator receiving power from the secondary transformer winding and generating data to be transmitted by the optical data transmitter;

a tube rotatably supported by the support structure, a proximal end of the tube connected to the signal generator and a distal end of the tube connected to the rotary pot core half; and a wire that electrically connects the signal generator to the secondary transformer winding, the wire passing through the tube from the proximal end to the distal end.

10. The input device of claim 9, wherein the signal generator generates a voltage signal to be transmitted by the optical data transmitter in response to the voltage provided by the secondary transformer winding.

11. The input device of claim 10, wherein the electric power source is connected to the optical data receiver, the electric power source being turned on and off in response to the voltage signal received by the optical data receiver.

* * * * *